(12) United States Patent
Nadolski et al.

(10) Patent No.: US 7,846,134 B1
(45) Date of Patent: Dec. 7, 2010

(54) FLEXIBLE WALLED CANNULA

(76) Inventors: Timothy Nadolski, 3845 Corporate Centre Dr., O'Fallon, MO (US) 63368; Carl Awh, 250 Ensworth Pl., Brentwood, TN (US) 37205; Jeffrey R. Diekemper, 3845 Corporate Centre Dr., O'Fallon, MO (US) 63368

( * ) Notice: Subject to any disclaimer, the term of this patent is extended or adjusted under 35 U.S.C. 154(b) by 777 days.

(21) Appl. No.: 11/821,326

(22) Filed: Jun. 22, 2007

Related U.S. Application Data

(60) Provisional application No. 60/816,065, filed on Jun. 23, 2006.

(51) Int. Cl.
 *A61M 5/178* (2006.01)
(52) U.S. Cl. .................................. 604/164.11
(58) Field of Classification Search ............ 604/164.01, 604/164.02, 164.03, 164.04, 164.05, 164.06, 604/164.07, 164.09, 164.11
 See application file for complete search history.

(56) References Cited

U.S. PATENT DOCUMENTS

| | | | | |
|---|---|---|---|---|
| 5,292,324 | A * | 3/1994 | McDonald | 606/107 |
| 5,630,809 | A * | 5/1997 | Connor | 606/4 |
| 5,662,659 | A * | 9/1997 | McDonald | 606/107 |
| 5,697,947 | A * | 12/1997 | Wolf et al. | 606/185 |
| 6,361,520 | B1 * | 3/2002 | Rockley | 604/22 |
| 6,398,754 | B1 * | 6/2002 | Sutton et al. | 604/22 |
| 6,605,054 | B2 * | 8/2003 | Rockley | 604/22 |
| 6,936,053 | B1 * | 8/2005 | Weiss | 606/107 |
| 6,966,921 | B2 * | 11/2005 | Scheller et al. | 606/166 |
| 7,204,820 | B2 * | 4/2007 | Akahoshi | 604/22 |
| 2002/0091351 | A1 * | 7/2002 | Rockley | 604/22 |
| 2004/0133224 | A1 * | 7/2004 | Scheller et al. | 606/166 |
| 2004/0199171 | A1 * | 10/2004 | Akahoshi | 606/107 |
| 2004/0199192 | A1 * | 10/2004 | Akahoshi | 606/169 |
| 2004/0267211 | A1 * | 12/2004 | Akahoshi | 604/264 |
| 2005/0020990 | A1 * | 1/2005 | Akahoshi | 604/272 |
| 2006/0224174 | A1 * | 10/2006 | Smith et al. | 606/190 |
| 2008/0077164 | A1 * | 3/2008 | Murphy | 606/159 |
| 2008/0103514 | A1 * | 5/2008 | Dybbs | 606/166 |
| 2008/0215078 | A1 * | 9/2008 | Bennett | 606/166 |
| 2009/0005738 | A1 * | 1/2009 | Franer | 604/164.01 |
| 2010/0160851 | A1 * | 6/2010 | Dimalanta et al. | 604/22 |

* cited by examiner

*Primary Examiner*—Nicholas D Lucchesi
*Assistant Examiner*—Aarti B Berdichevsky
(74) *Attorney, Agent, or Firm*—Kevin L. Klug

(57) ABSTRACT

A flexible walled cannula apparatus and method of use comprising a uniquely deformable cannula tube and head in combination with a uniquely shaped obturator which allows the use of heretofore unusable larger gauge surgical instruments while providing a self sealing incision. The apparatus and method of use provides a preassembled obturator and cannula assembly with which the surgeon forms an incision or channel, inserts the cannula tube, and through the cannula inserts surgical instruments to perform a surgical operation. The apparatus and method of use is especially suited for ophthalmic surgical operations. Alternative embodiments for use with even larger diameter instruments utilize a uniquely designed valve having leaflets which prevent bodily or other fluid leakage from the cannula when an instrument is not inserted.

19 Claims, 10 Drawing Sheets

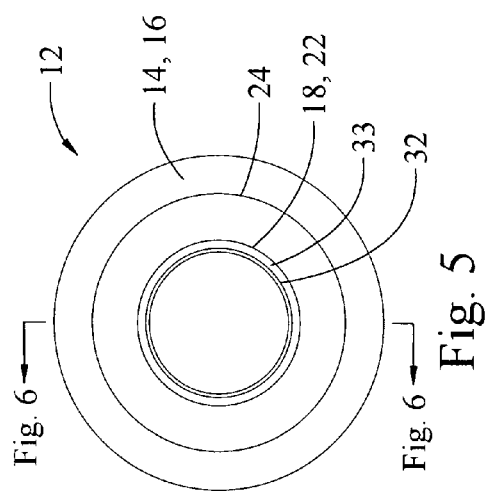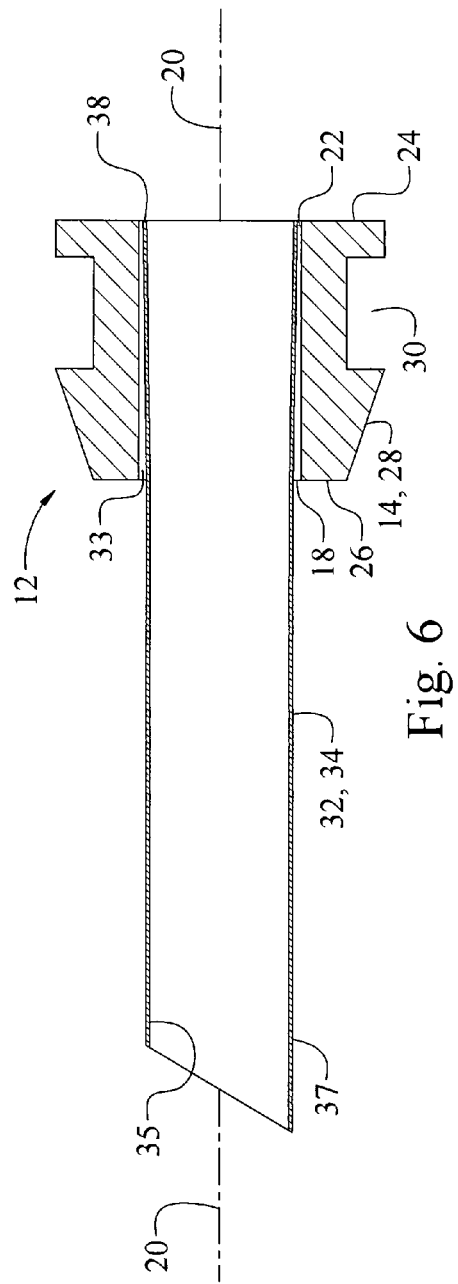

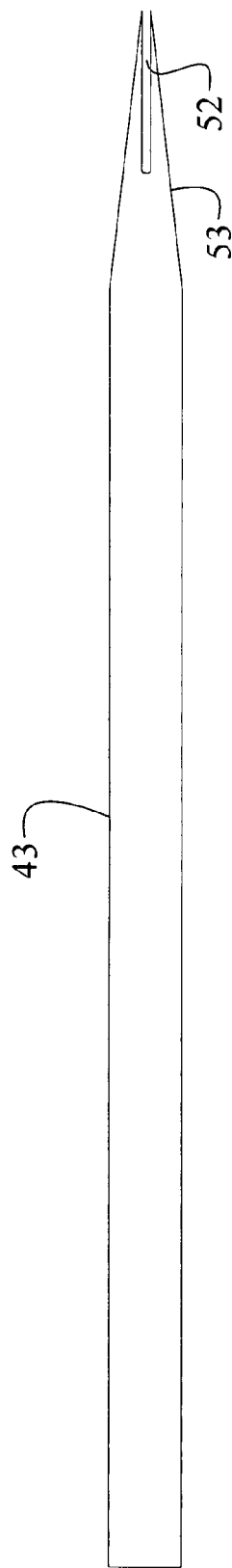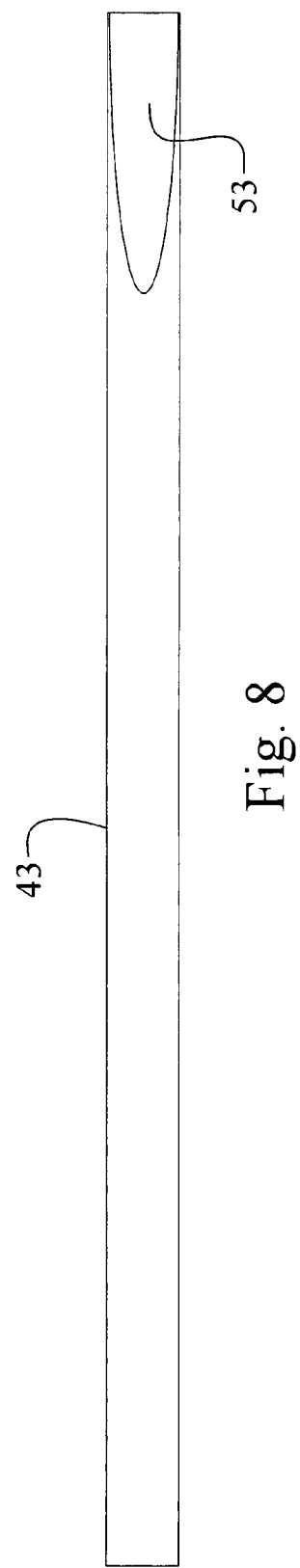

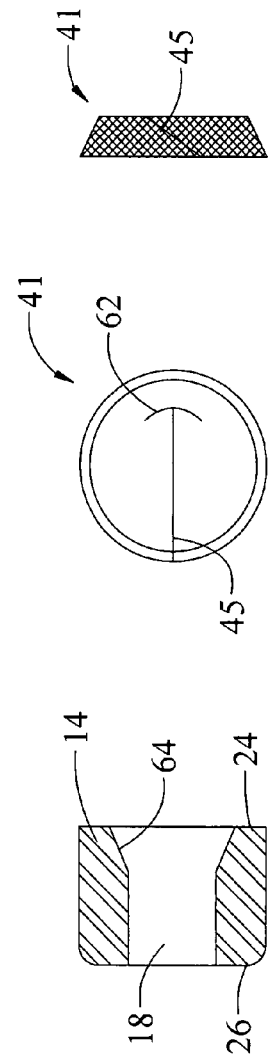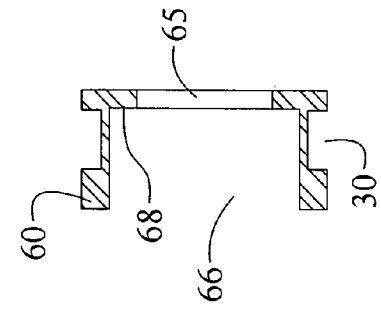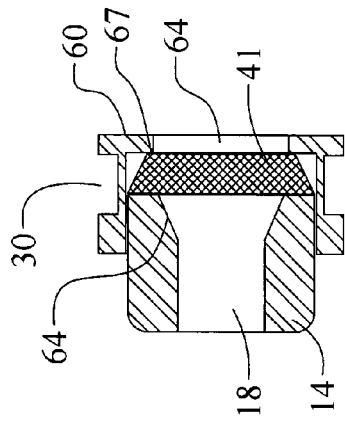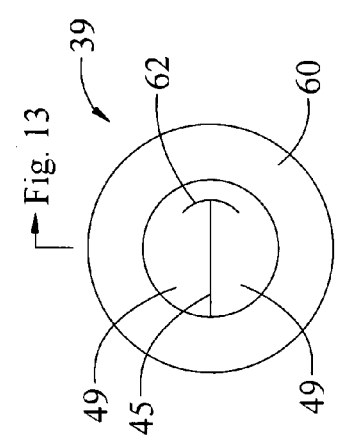

FLEXIBLE WALLED CANNULA

This application claims priority of U.S. Provisional Patent Application No. 60/816,065, entitled Flexible Walled Cannula filed Jun. 23, 2006.

BACKGROUND OF THE INVENTION

The art of the present invention relates to surgical instruments and cannulas for surgical use and more particularly to a flexible cannula which substantially seals with or within an incision and allows a surgical instrument of a width or dimension greater than the inside round undeformed diameter of the cannula to fit through the cannula via elastic deformation of said cannula while continually sealing the incision through which said cannula is placed. The present art utilizes a combination of a uniquely modified microvitreoretinal blade or obturator assembled in conjunction with the flexible cannula whereby a self sealing and substantially flat incision is created for placement and use of said cannula. The substantially flat incision in combination with the flexible cannula allows a surgeon to create a larger incision which accommodates a larger instrument (such as a 20 gauge surgical instrument) through said cannula, all while maintaining the desirability of a self sealing incision. The art of the present invention is especially useful during ophthalmic or eye surgeries.

Prior art devices and methods utilize generally inflexible or rigid cannulas to introduce instrumentation within or into an organ during surgery, including but not limited to surgeries within the globe of the eye. Typically, the prior art is manufactured from a substantially rigid polyimide or stainless steel material or tubing which does not easily accommodate the deformation necessary for insertion of an instrument that violates the envelope (i.e. inside diameter) of the cannula tube or tubing. A conventional cannula typically consists of a head and a cannula tube or tubing and often has a trocar or sharp instrument portion on said tube in order to puncture or insert into a body organ. The head serves to position or stop the cannula at the correct insertion depth. Said head also serves to guide the surgical instrument into said cannula tube and further provides for convenient removal of the cannula following a surgical procedure. That is, the head is easily grasped for removal. During surgeries of the eye, the cannula tube is the passageway through the eye wall that allows a surgical instrument access to the interior regions of the eye globe. Prior art methods of attaching or mounting the cannula tube with the cannula head also limited cannula deformation and thereby limited the ability the cannula to accommodate an instrument which violates the cannula envelope.

Prior art cannula methods of use often create an incision with a hypodermic needle or beveled wire utilized as an obturator prior to cannula insertion. The needle creates a circular hole or semi-circular incision within the body organ into which the substantially non-flexible cannula is inserted. Said circular hole or semi-circular incision is required for insertion and accommodation of non-flexible cannulas. Unfortunately, said circular or semi-circular incision is generally not self sealing when the cannula is removed, except for approximately 25 gauge incisions. This is especially true for larger cannula sizes such as 20 gauge. If the incision, hole, or wound is not self sealing, sutures are required to close the wound, which procedure is generally more invasive and traumatic to the patient.

Cannula systems minimize trauma to the surrounding tissue during surgery as the incision remains open and protected. This advantage is especially useful during retinal surgeries as instruments are continuously introduced, manipulated, and removed through an incision within the eye globe or through the sclera. Often cannulas, including the head and tube portions, are sized for insertion of 20, 23, and/or 25 gauge instruments with other sizes available.

Conventional cannula limitations require that instruments introduced there through are smaller than or do not violate the envelope defined by the inner diameter walls of the cannula tube or head. The present art utilizes an extremely thin wall tubing that purposely deforms around the introduced surgical instrumentation and allows deformation of the incision without harm to said incision. The present art also utilizes a uniquely designed microvitreoretinal (MVR) type blade or obturator in combination with the deformable cannula. That is, the present art comprises a head and cannula tube with said cannula tube or tubing attached with or to said head whereby the cannula tubing retains the ability to elastically deform, all of which is assembled onto a shaft of a unique MVR blade or obturator which provides a substantially flat incision and easy insertion of the cannula. Said elastic deformation allows introduction of instruments through said cannula tube which are unable to fit through prior art devices. This is especially true for flattened instruments such as MVR blades whereby the flexible cannula tube allows a smaller incision to accommodate a wider instrument which heretofore required a larger more traumatic incision.

The deformable cannula tube and method of use of the present art is also less traumatic on the eye wall and scleral tissue during ophthalmic surgeries since the present art substantially closes or seals when an instrument is not inserted there through and into the eye. That is, the present art method of use utilizes a "slit" or substantially flat incision (typically formed with the described obturator) instead of a circular hole typically created by a hypodermic needle or trocar. The sealing or closing substantially reduces or eliminates the requirement for incision plugs as leaking from the organ, especially the eye, is substantially eliminated when the deformable cannula of the present art pinches closed. The present art apparatus further allows cannula insertion with or via the incision created by a substantially flat yet modified MVR blade or obturator. That is, when fed through the flexible cannula tube prior to surgical placement, the uniquely combined MVR blade or obturator may create the incision, insert the cannula placed upon the shaft of said obturator, and thereafter be removed from or back through the flexible tube whereby further instruments may be introduced through said cannula. The present art apparatus and method of use eliminates the multi-step requirement of creating an incision tangential to the sclera with an MVR blade or hypodermic needle, removing the blade, then inserting an appropriately sized trocar into the incision to accommodate the cannula tube size. With the current prevalence of 23 gauge (and larger with the present art valved embodiment) non-suture surgery, single step cannula insertion is less traumatic and substantially quicker and more convenient.

The art of the present invention may be used in and with many types of surgical procedures, especially including but not limited to ophthalmic procedures.

Accordingly, it is an object of an embodiment the present invention to provide a flexible walled cannula having a deformable cannula tube which accommodates an instrument of a greater width than the tube inside diameter without injury to the surgical site or patient.

Another object of an embodiment of the present invention is to provide a flexible walled cannula which when used with the present art obturator substantially closes or seals at the insertion site when an instrument is not inserted through the apparatus.

A further object of an embodiment of the present invention is to provide a flexible walled cannula apparatus and method of use which allows a surgeon to insert the cannula in conjunction with a specially formed obturator and provide a substantially automatic seal at the insertion site without the use of specialty cannula plugs when the obturator is removed.

A still further object of an embodiment of the present invention is to provide a flexible walled cannula combined with an obturator as an apparatus and method of use which promotes post surgical healing via utilization of a slit or substantially flat incision instead of a prior art circular hole and is minimally invasive to the patient.

A yet further object of an embodiment of the present invention is to provide a flexible walled cannula combined with an obturator as an apparatus and method of use which allows a surgeon to utilize larger diameter (i.e. lower gauge) instruments than previously have been commonly used, while maintaining a desirable self sealing incision.

SUMMARY OF THE INVENTION

To accomplish the foregoing and other objects of the embodiments of this invention there is provided a flexible walled cannula apparatus and method of use in combination with an obturator especially designed for use with and during ophthalmic surgery. Although the apparatus is especially suited for use with and during ophthalmic surgery it may be utilized with and during a plurality of other surgical procedures. As aforesaid, the present art provides embodiments that when compared with the prior art uniquely allows use of larger width instruments through smaller slits or flat incisions than previously have been commonly used, reduce fluid leakage when the instrument is removed from the cannula (i.e. vitreous humor, aqueous humor, or saline during ophthalmic surgery), further reduce the requirement for sutures after the cannula is removed, reduce trauma to the surgical site due to the small slit incision size utilized for the cannula, and thereby promotes a faster healing of the surgical site.

The present art comprises a cannula having a head which can be of a plurality of shapes or forms with a connected or attached cannula tube of a flexible material all in combination with an obturator or modified MVR type blade specially designed for use with said cannula. Said head may be manufactured from a plurality of materials including but not limited to metals and alloys thereof, rubbers, plastics, woods, composites, ceramics, or a combination thereof. Preferably said head is of a round button like shape with an orifice communicating there through and into which is mounted said cannula tube. Preferably said head is manufactured from a flexible rubber or polymer like material. That is, in an embodiment of the present art, the deformable head also flexes during insertion of an instrument.

In the preferred embodiment, said head is substantially circular in cross section in a plane substantially perpendicular to the lengthwise axis of said orifice and has a first proximal end and a second distal end from which said cannula tube extends. That is, the second distal end is the end from which said cannula tube extends with the outside diameter of the cannula tube held within said orifice. Near or at said second distal end and external to the head is a substantial taper from near or at said cannula tube which tapers to a greater overall head diameter as said taper runs toward said first proximal end. Between said first proximal end and said greater diameter end of said taper is a substantially circumferential slot or groove. Said orifice runs from said first proximal end through said second distal end and may vary in diameter along said run. Said cannula tube may be inserted fully or partially within said orifice.

Said flexible material cannula tube is a substantially tube form and may be manufactured from a plurality of substantially flexible materials including but not limited to polytetrafluoroethylene (PTFE), fluorinated ethylene propylene (FEP), perfluoroalkoxy (PFA), polyethylene terephthalate (PET), polyetheretherketon (PEEK), a flexible polyimide, or a combination thereof. Preferably said flexible cannula tube is formed from a polyimide tubing but may also be formed via a heat shrink form of the aforesaid materials onto a sizing mandrel. The flexible cannula tube may also be formed into or onto said head or extruded as a thin wall tubing which is attached within said orifice via adhesives including but not limited to a cyanoacrylate. Said cannula tube may also be pressed or frictionally fit, molded, or held via fasteners with said head. As aforesaid, said cannula tube exits or transitions from said second distal end of said head.

An alternative embodiment creates a step in said cannula tube or tubing, i.e. non-uniform inside diameter, whereby a larger diameter is nearest or at said cannula head for easy instrument insertion and a smaller outside diameter of said flexible tube is inserted through the organ wall, i.e. the eye wall or sclera during ophthalmic surgery. A further embodiment utilizes a cannula tube flared region at said head instead of a step whereby the ease of instrument insertion is provided. A still further alternative embodiment provides an oversized opening in said head for accommodation of said instrument yet further flexibly attaches said cannula tube to said head whereby desirable tube deformation is provided. That is, the orifice may be of a greater diameter than the outside diameter of the cannula tube whereby the cannula tube may deform within the orifice of the head.

The obturator of the present art in combination with the cannula uniquely allows a surgeon to form an incision, insert the cannula, and remove the obturator in a manner that is quicker and less traumatic than in the prior art. The blade portion of the present art obturator has a dulled side and a protrusion opposite the dulled side along with a cutting edge. The cutting edge ensures a slit or substantially flat incision while the dulled side and protrusion protects the cannula from cutting edge damage during cannula insertion and obturator withdrawal.

For larger instruments (i.e. smaller gauge size), the present art utilizes one or more valves in conjunction with the cannula in order to ensure a seal when the cannula is placed. Limitations of a pinch or compression seal of the cannula tube are found when instruments of approximately 20 gauge are utilized with the present art cannula. An embodiment of the present art places a flexible sheet material having a slit onto or with the cannula head which provides one or more leaflets which seal the cannula and thereby function as a valve. The sheet material has a preferable disc form and is partially covered with a cap, both of which are preferably adhesively attached with the head. In a preferred embodiment, the slit in the sheet is of an arcuate semi-circular form with an at least partially perpendicular (to a tangent of the arc) cut towards the edge of the disc. The valve portion, including the sheet with a slit, reduces any fluid leakage from the organ yet provides a surgeon with the flexibility to utilize larger diameter or width surgical instruments. Preferably, said sheet material valve is formed from a silicone sheet material but for alternative embodiments may be formed from any one or more of a plurality of bio-compatible flexible materials.

When used in conjunction with the valve, in an embodiment, the obturator of the present art has a notched or reduced diameter portion which serves as a seat for the valve when the obturator is inserted through the cannula. In such a position, one or more of the formed valve leaflets mate with the notch to allow a less deformed position for the leaflets than when such leaflets are positioned on the larger diameter portion of the obturator. In a preferred embodiment, the notched portion allows the valve to maintain a substantially relaxed position prior to cannula use, which assists in producing a positive valve seal and thereby allows reduced fluid leakage when such cannula is in use. One or more of the formed valve leaflets mate with the notch to provide an optimum fluid seal.

The art of the present invention may be manufactured from a plurality of materials including but not limited to those listed without departing from the scope and spirit hereof, intended provided the essential physical attributes are maintained. The apparatus may further be manufactured via molding, machining, casting, pressing, laminating, carving, or utilization of stereo-lithographic or electro-dynamic milling or other techniques which are appropriate for the material utilized.

BRIEF DESCRIPTION OF THE DRAWINGS

Numerous other objects, features and advantages of the invention should now become apparent upon a reading of the following detailed description taken in conjunction with the accompanying drawings, in which:

Numerous other objects, features and advantages of the invention should now become apparent upon a reading of the detailed description taken in conjunction with the accompanying drawings, in which:

FIG. 5 is a rear plan view of an alternative embodiment flexible walled cannula showing an orifice larger than the outside diameter of the cannula tube.

FIG. 6 is a cross sectional plan view taken along line 6-6 of FIG. 5.

FIG. 7 is a top plan view of the preferred embodiment of the obturator shaft.

FIG. 8 is a right side plan view of the preferred embodiment of the obturator shaft.

FIG. 12 is a top plan view of the alternative embodiment valve of the present invention.

FIG. 13 is a cross sectional view taken along line 13-13 of FIG. 12.

FIG. 14 is a cross sectional view taken along line 13-13 of FIG. 12 which includes only the cap.

FIG. 15 is a top plan view of the alternative embodiment head utilized with the alternative embodiment valve.

FIG. 16 is a cross sectional view taken along line 16-16 of FIG. 15.

FIG. 17 is a top plan view of the sheet or disc of the alternative embodiment valve.

FIG. 18 is a left side plan view of the sheet or disc of the alternative embodiment valve showing the slit or perpendicular cut.

DETAILED DESCRIPTION

Figure 1:
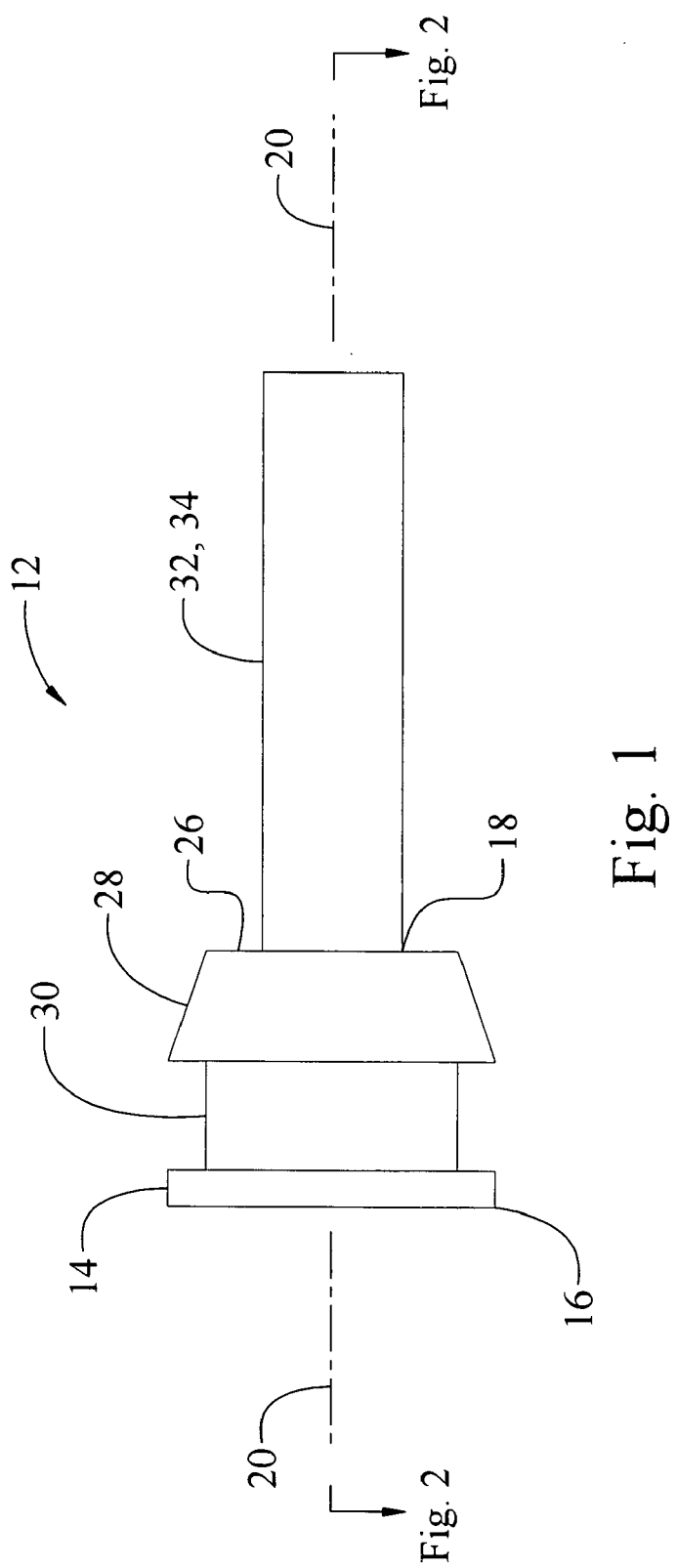
FIG. 1 is a right side plan view of a preferred embodiment of the flexible walled cannula.
Figure 2:
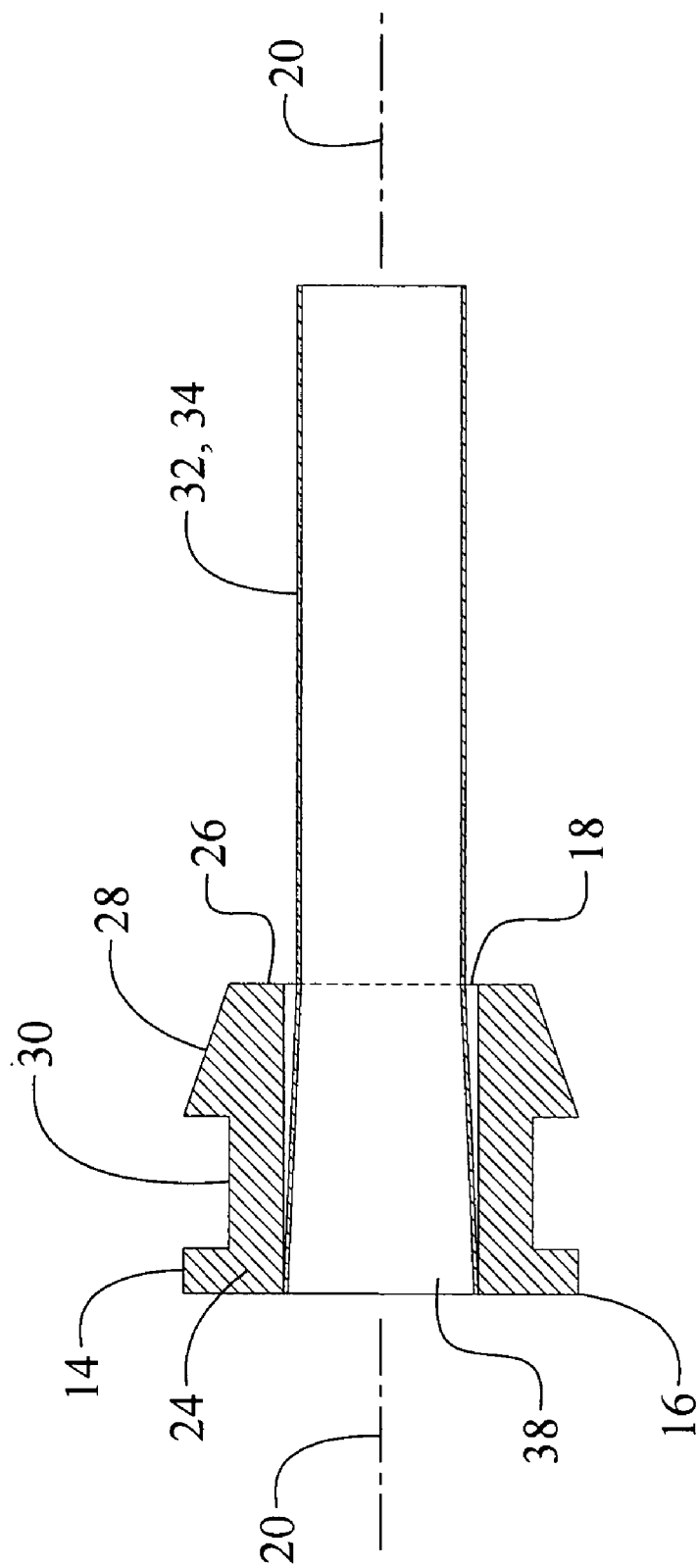
FIG. 2 is a cross sectional plan view taken along line 2-2 of FIG. 1.
Figure 3:
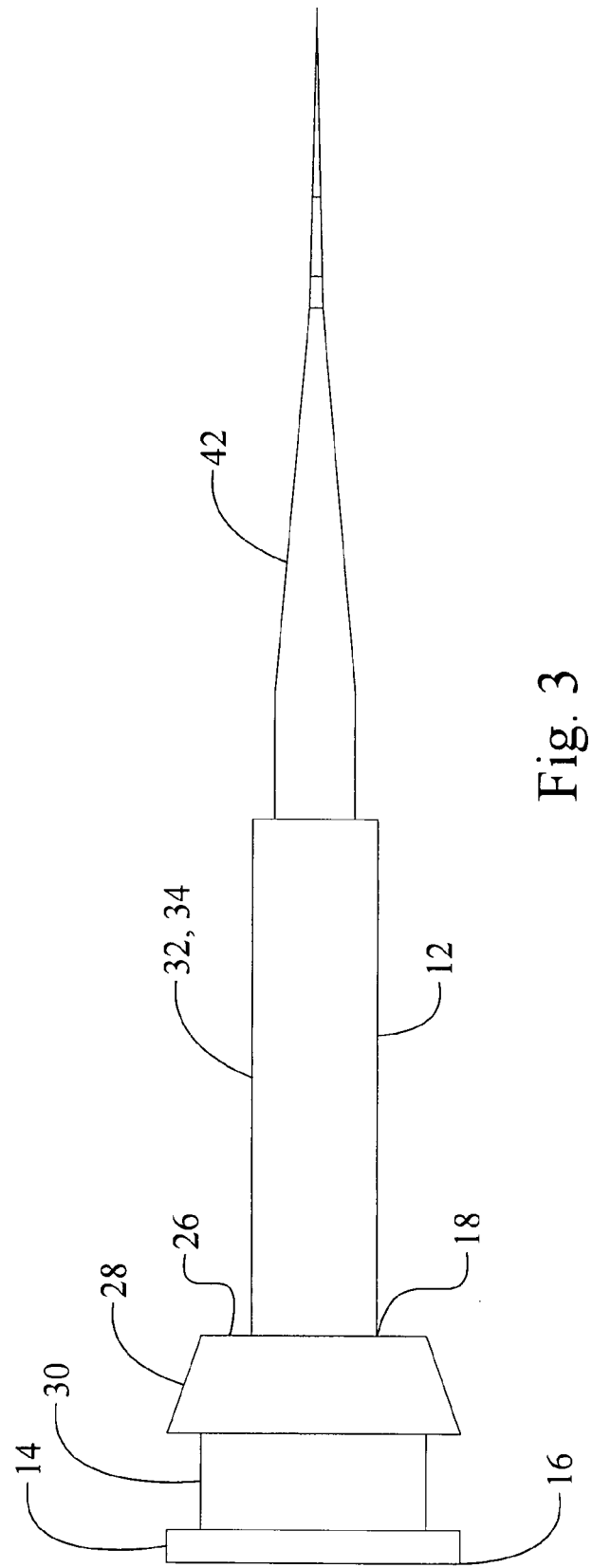
FIG. 3 is a right side plan view thereof with an obturator extending therefrom.
Figure 4:
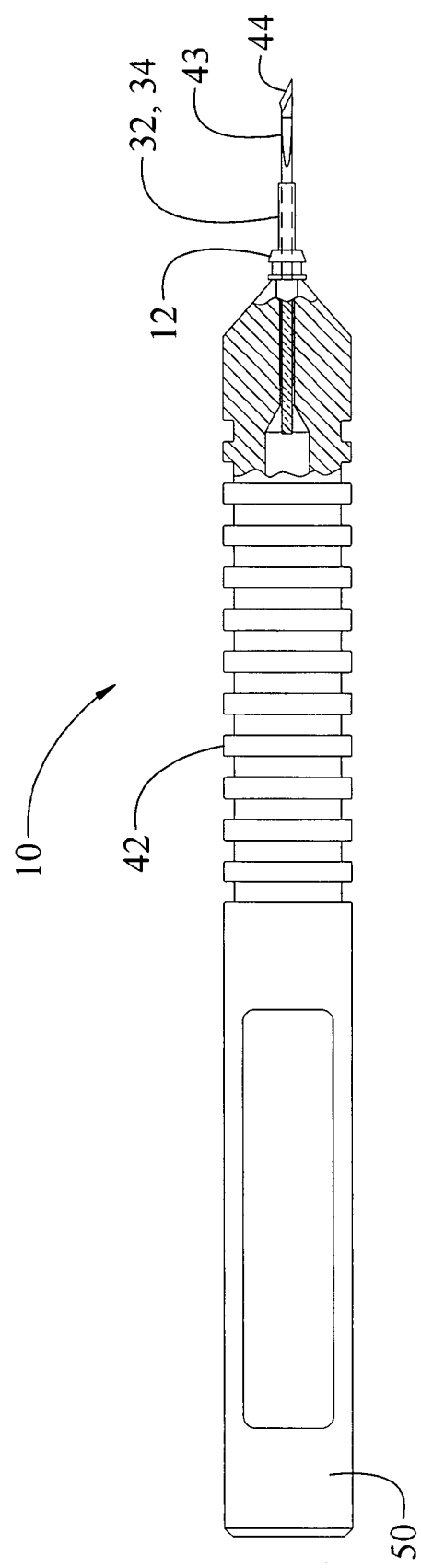
FIG. 4 is a right side plan partial cross sectional view of an obturator with handle and a preferred embodiment flexible walled cannula fitted over said obturator.
Figure 9:
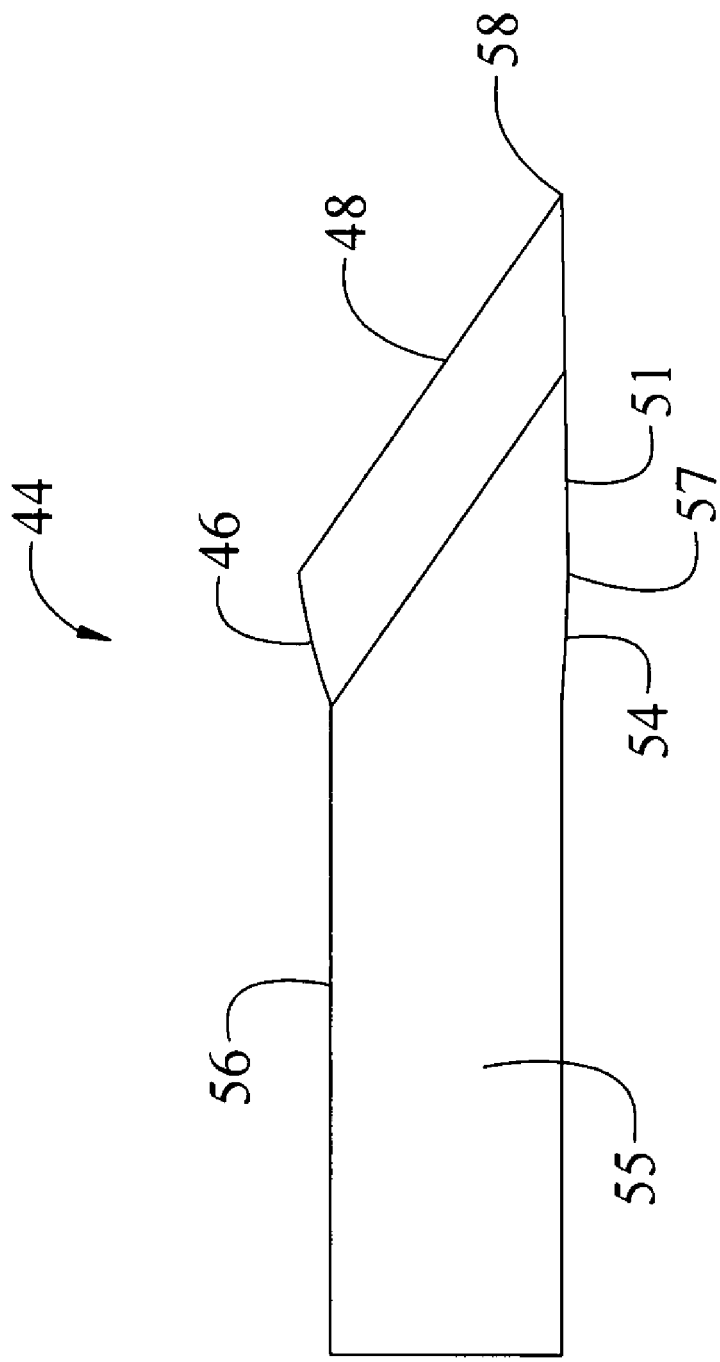
FIG. 9 is a right side plan view of the preferred embodiment of the obturator blade portion.
Figure 10:
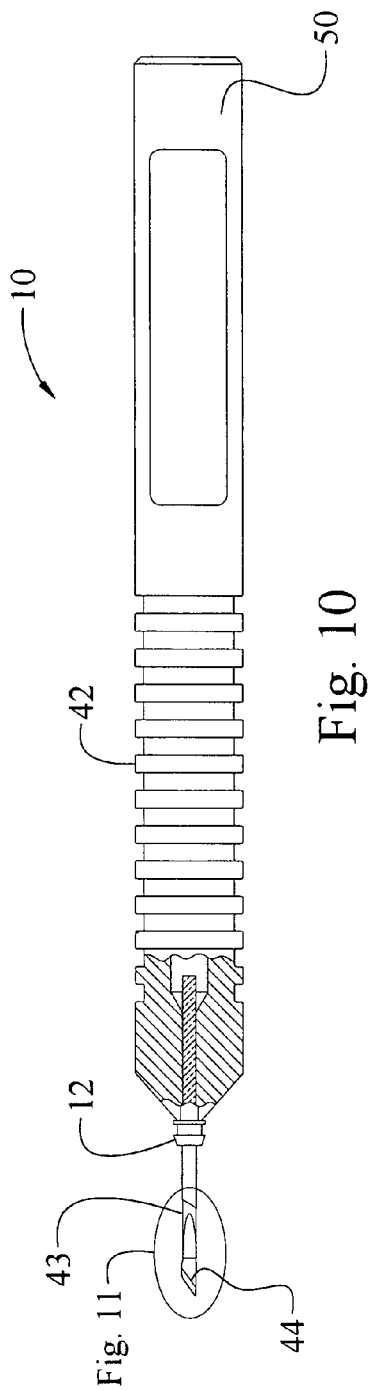
FIG. 10 is a left side partial X-ray view of the alternative embodiment cannula placed onto an obturator showing the handle, shaft, and blade portion.
Figure 11:
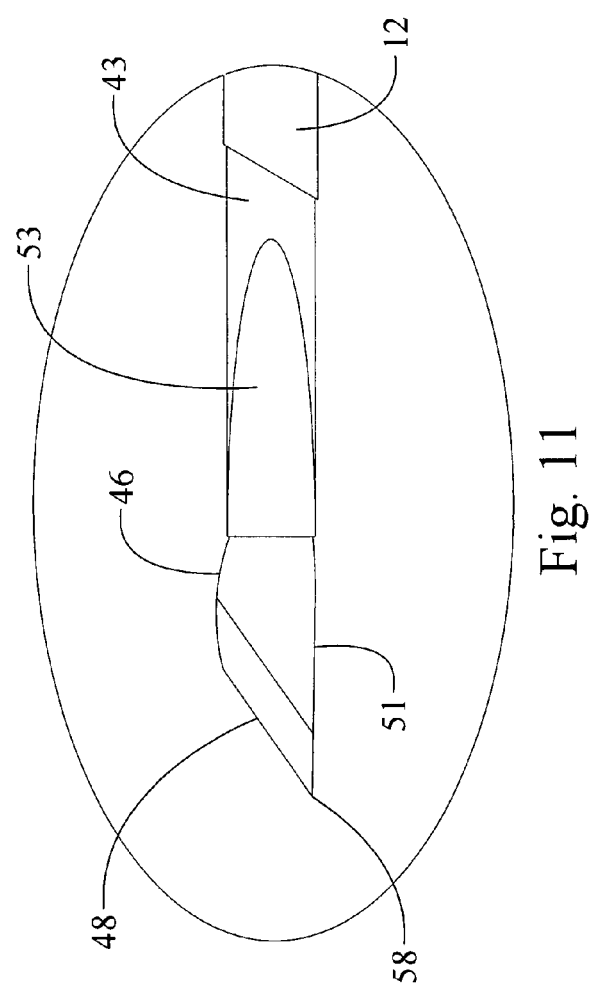
FIG. 11 is an enlarged view of the circled portion in FIG. 10 showing the blade inserted and attached with the shaft.
Figure 19:
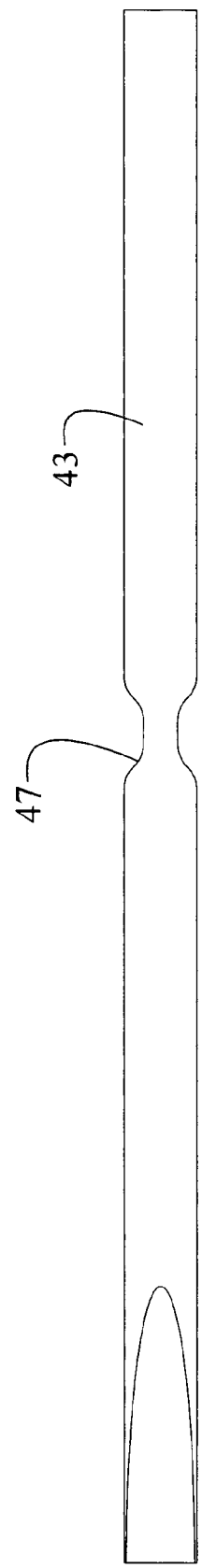
FIG. 19 is a right side plan view of the obturator shaft showing the notch or groove.

Referring now to the drawings, there is shown in FIGS. 1-4, 7-9 a preferred embodiment of the flexible walled cannula 10 of the present art and in FIGS. 5, 6, 10 & 11 an alternative embodiment of the present art showing the cannula 12 and obturator 42 and in FIGS. 12-19 an alternative embodiment showing the cannula valve 39 and associated elements thereof.

The preferred embodiment of the present art comprises a cannula 12 having a head 14 which can be of a plurality of shapes or forms with a connected or attached cannula tube 32 of a flexible or elastic material, all in combination with a uniquely formed obturator 42 which shares some similarities with a conventional microvitreoretinal (MVR) blade. Said head 14 may be manufactured from a plurality of materials including but not limited to metals and alloys thereof, rubbers, plastics, woods, composites, ceramics, or a combination thereof, or any suitable material. Preferably said head 14 is of a round button like shape 16, preferably manufactured from a flexible rubber like material, with an orifice 18 having one or more diameters communicating there through. Within at least a portion of said orifice 18 is mounted said cannula tube 32. The deformable head 14, when manufactured from a flexible material, also flexes during insertion of an instrument. In an embodiment, the cannula is a unitary device comprising a head portion and a tube portion, the portions of such unitary device configured similarly to the head 14 and tube 32 of the preferred embodiment described below.

In the preferred embodiment, said head 14 has a substantially circular cross section in a plane substantially perpendicular to an axis 20 of said orifice 18 and has a first proximal end 24 and a second distal end 26 and is at least partially attached with said cannula tube 32. The second distal end 26 represents the head 14 portion from which said cannula tube 32 extends. On the exterior of said head 14 near or at said second distal end 26 is a substantial taper 28 from near or at said cannula tube 32 which tapers to a greater overall head 14 diameter as said taper runs toward said first proximal end 24. Between said first proximal end 24 and said greater diameter end of said taper 28 is a substantially circumferential slot or groove 30 which allows a surgeon to grasp the cannula 12 with a forceps or similar instrument during insertion and removal. Said orifice 18 runs from said first proximal end 24 through said second distal end 26 and may vary in diameter along said run.

Said flexible material of the deformable cannula tube 32 has a substantially tubular form 34 and may be manufactured from a plurality of substantially flexible materials including but not limited to polytetrafluoroethylene (PTFE), fluorinated ethylene propylene (FEP), perfluoroalkoxy (PFA), polyethylene terephthalate (PET), polyetheretherketon (PEEK), polyimide or a combination thereof. Preferably said flexible or deformable cannula tube 32 is formed via a heat shrink form of one or more of the aforesaid materials onto a sizing mandrel or into or onto said head 14 or extruded as a thin wall tubing which is attached within said orifice via an adhesive, including but not limited to cyanoacrylate. Press or frictional fits, integral molding, or fasteners may be used to connect the cannula tube 32 with said head 14. As aforesaid, said cannula tube 32 exits or transitions from said second distal end 26 of said head 14 and extends therefrom for insertion into an anatomical organ such as the eye. That is, during ophthalmic surgery, the tube 32 is inserted through the eye wall or sclera. An alternative embodiment of the distal end of the cannula tube 32 is cut at an approximately 30 degree angle relative to a plane perpendicular to the cannula tube 32 lengthwise axis 20. Alternative embodiments may utilize a plurality of distal end cut angles. Such cut angles may assist the insertion of said cannula tube 32 through the organ. Further alternative embodiments may utilize a cannula tube 32 which is not circular in cross section but instead may take any cross sectional form including but not limited to triangular, hexagonal, octagonal, or any polygonal or non-polygonal form, including a flat form.

The preferred embodiment utilizes a slightly flared or larger diameter 38 cannula tube 32 inside diameter 35 nearest said first proximal end 24 of the head 14. This flared region 38 promotes easy instrument insertion. An alternative embodiment creates a step in said cannula tube 32 or tubing, i.e. a non-uniform inside diameter, whereby a larger diameter is nearest or at said cannula head 14 for easy instrument insertion and a smaller outside diameter 37 of said tube 32 is inserted into the organ. A still further alternative embodiment provides an oversized opening 22 in said head 14 for accommodation of said instrument yet further flexibly attaches said cannula tube 32 with said head 14 whereby desirable tube deformation is provided. The aforesaid utilizes an oversized orifice 18 opening 22 in the head 14 and fills part or all of the void between the cannula tube 32 outside diameter 37 and the orifice 18 with a flexible adhesive such as cyanoacrylate.

Unique to the apparatus 10 and method of use is the combination of the oversized and modified microvitreoretinal (MVR) blade or obturator 42 and the cannula 12 structure. That is, the blade portion 44 width of the obturator 42 is larger than the inside diameter of the cannula tube 32 when not deformed. Creating an incision with the wider obturator 42 blade portion 44 allows a flatter or more slit like incision than the prior art as the blade portion 44 is substantially flat with a distal cutting edge 48. This wider incision allows use of 20 gauge instruments through the cannula yet provides a highly desirable self sealing cannula 12 insertion or incision point. That is, since the incision is more slit like and not half circular, the wound tends to self seal, yet the instrument size useable with the present art 10 is larger. Prior art 20 gauge cannula devices require use of semi circular or circular incisions, often created with a hypodermic needle, which required sutures to seal. The circular or semi-circular incision limited the size of the incision for self sealing and thereby limited the self sealing instrument size to approximately 23 gauge.

The present art combination of cannula 12 and obturator 42 provides a method by which the surgeon inserts the obturator 42 with the cannula head 14 and tube 32 placed or inserted onto the shaft 43 of the obturator 42 into the tissue at the surgical site, i.e. through the sclera during ophthalmic surgery. Prior to surgery, the cannula tube 32 (i.e. inside diameter 35) is moveably or slidably mounted upon the obturator 42 shaft 43. After insertion of the obturator 42, the cannula 12 is then pushed into the incision (preferably with forceps grasping the slot or groove 30) and the obturator 42 is removed. Further surgical instruments may then be inserted and removed through the cannula head 14 and tube 32 during the surgical procedure without harming the surrounding tissues protected by the cannula 12.

In a preferred and alternative embodiment, the head 14 has an oversized orifice 18 into which said cannula tube 32 is inserted. The space between the cannula tube 32 and orifice 18 is at least partially filled or surrounded by a flexible adhesive 33 such as a cyanoacrylate. The orifice 18 has a diameter which is approximately as large or larger than the width of the blade portion 44 of the obturator 42 with the flexible adhesive 33 filling at least part of the void between the orifice 18 and the tube 32 outside diameter 37. This configuration allows for insertion of the obturator 42 into and out of the orifice 18 of the head 14, even if the head 14 is of a more rigid material, while further allowing the cannula tube 32 to distort, flex, or deform as the blade portion 44 of the obturator 42 is inserted or removed therefrom. That is, the blade portion 44 has a width greater than the inside diameter 35 of the undeformed cannula tube 32 and the clearance between the diameter of the orifice 18 and the tube 32 outside diameter 37 allows the tube 32 to flex or deform within the orifice 18.

In an embodiment, the modified MVR blade or obturator 42 utilized in the unique combination of the present art flexible walled cannula 10 has a handle 50, a shaft 43 mounted with said handle 50, and a blade portion 44 with a unique specialized form which is mounted distally with said shaft 43. In a preferred embodiment, the shaft 43 has a first proximal end inserted and/or held with said handle 50 and a second distal end having a slit 52 into which the blade portion 44 is inserted and held. Preferably, the blade portion 44 is laser welded with the shaft 43 after insertion into said slit 52. Said shaft 43 has a taper 53 at said second distal end in order to provide a smooth transition to the blade portion 44. In an alternate embodiment the shaft 43 comprises the blade portion 44 so that no weld is required there between.

In a preferred embodiment, the blade portion 44 is of a substantially flat form and has a base 55 and a distal cutting edge 48 which is preferably formed or ground at an angle relative to the shaft 43 lengthwise axis. The blade portion 44 has a dulled bump or protruded 46 portion extending from a top side 56 of said blade portion 44 which forms a heel like structure relative to the cutting edge 48. The bump or protruded 46 portion is located proximally from the cutting edge 48 portion. This bump or protruded 46 portion minimizes the probability of the obturator 42 cutting or piercing the cannula 12 during retraction from the cannula 12. The blade portion 44 also has a bottom side 54 which is substantially dulled in order to also minimize the probability of cannula 12 cutting or piercing during retraction. The preferred embodiment also has a slight raised portion 57 on the bottom side 54 which slightly offsets the cutting edge 48 tip 58 from the bottom side 54 and towards the top side 56 in order to further minimize any cannula 12 cutting or piercing.

The obturator 42 is inserted through the cannula 12 to form the flexible walled cannula 10 assembly prior to use. That is, the insertion is through the orifice 18 and the cannula tube 32 with the cannula tube 32 deforming as the blade portion 44 transgresses there through. (also through the valve 39 in an alternative embodiment) This insertion is preferably performed under microscopic observation whereby a cutting or tearing of the cannula tube 32 by the cutting edge 48 is avoided. Prior to a surgical procedure, the cannula 12 with said head 14 and cannula tube 32 rests upon the shaft 43 of the obturator 42. Once assembled, the flexible walled cannula 10 assembly is ready to initiate the surgical procedure.

Procedure initiation begins with the surgeon forming an incision with the cutting edge 48 of the blade portion 44 and inserting the blade portion 44 into the anatomical organ. For ophthalmic surgery, this step provides a channel through the sclera and/or choroid which communicates with the vitreous humor. After insertion, the cannula tube 32 is inserted into the anatomical organ by sliding the cannula 12 into said incision or channel while said cannula 12 is guided by said shaft 43. That is, the cannula tube 32 fits or inserts into the incision and the head 14 serves to limit the depth of insertion upon contact with the surface of the anatomical organ. During ophthalmic surgery, the head contacts the sclera and prohibits further insertion of the cannula tube 32 into the vitreous humor.

The obturator 42 is then removed from the cannula 12 whereby additional instruments are inserted though the cannula 12 in order to proceed with the surgical procedure. Since the cannula tube 32 is flexible or deformable within the substantially flat incision of the obturator 42, upon removal of the obturator 42, the inside diameter 37 of the cannula tube 32 substantially pinches closed and substantially seals. This prevents vitreous material from exiting when an instrument is not inserted through the cannula 12. Although the present art is substantially self sealing, circumstances may arise when insertion of a cannula plug may be necessary at the first proximal end 24 of said head 14. This is especially true with patients having a high intraocular pressure during ophthalmic surgery.

The surgeon proceeds with the surgery via insertion and removal of one or more instruments through said cannula 12 and into the anatomical organ. Upon completion of the surgery, the cannula 12 is removed via placement of a removal force upon the head 14, typically via a forceps mated with said slot or groove 30. The substantially flat or linear incision first created by the obturator 42, barring unexpected circumstances, self seals without the necessity of sutures. Although self sealing incisions have been utilized in the past, the aforesaid method of using the present apparatus allows a surgeon to employ instruments having shaft sizes greater than those previously used during self sealing surgical procedures. (i.e. 20 gauge or larger instruments) That is, a substantially flat incision can be larger or longer than the prior art half or full circular incision diameter (i.e. formed by a hypodermic needle or trocar) without leakage. The unique combination of the present art blade portion 44 and the cannula tube 32 flexibility ensures a reliable surgical utilization of the flexible walled cannula 10 without the risk of a cannula tube 32 cuts or tears during obturator 42 removal.

As the cannula tube 32 inside diameter 35 increases for accommodation of larger instrument shaft sizes the cannula 12 cannot self seal. That is, although the flat or linear incision will self seal upon completion of the surgical procedure, the inside diameter 35 of the cannula 12 inserted into the incision will not self seal. An alternative embodiment of the present art utilizes one or more uniquely formed valves 39 in the form of a sheet or disc 41, preferably of a silicone or other flexible material, preferably having an arcuate cut 62 and a slit cut 45 through which the surgical instrument is placed. The sheet 41 and cut 45, 62 combination forms one or more sealing leaflets 49 which conform to the surgical instrument shaft during use and seal when the instrument is removed. The valve 39 is placed onto or in said head 14 in a preferred alternative embodiment, yet may be placed within said cannula tube 32 for further alternative embodiments. When an instrument is removed from between the leaflets 49, the leaflets 49 substantially mate or close to form a seal, thereby preventing bodily or other (such as saline) fluid leakage.

One example of the aforesaid alternative embodiment head 14 with the valve 39 comprises a head 14 having a bevel 64 at the first proximal end 24 within the orifice 18, said sheet or disc 41, and a cap 60 which fits over said first proximal end 24 and sandwiches said sheet or disc 41 there between. The bevel 64 provides clearance for the sheet or disc 41 when an instrument is passed through the valve 39 and the sheet or disc 41 elastically deforms toward the orifice 18. In a preferred embodiment, the sheet or disc 41 has an off center placed semi-circular or arcuate cut 62 and a connecting radial or linear cut 45 through the sheet or disc 41 which is substantially perpendicular to a tangent of the semi-circular or arcuate cut 62. The radial cut 45 is angled relative to the plane of the sheet or disc 41 in order to form overlapping leaflets 49 which ensure a seal and preferably extends to the edge or periphery of the sheet or disc 41. Alternative embodiments may place the two cuts 45, 62 in a non-perpendicular fashion or not extend the radial cut 45 to the edge or periphery of the sheet or disc 41 provided the composite valve 39 is sufficiently large to accommodate the instrument size desired. Further alternative embodiments may utilize only a single cut or a plurality of cuts to form one or more valve 39 leaflets 49.

Assembly of the preferred alternative embodiment valve 39 proceeds with the modified head 14 having a bevel 64 at the first proximal end 24 as described. The sheet or disc 41 is preferably adhesively bonded or attached (preferably with a cyanoacrylate) with the head 14 first proximal end 24 and is sized to substantially match the diameter of said head 14. The cap 60 has a bore 66 which is of a substantially equivalent diameter as the head 14 diameter and is mated over the first proximal end 24 of the head 14 and adhesively bonded or attached thereto. (again, preferably with a cyanoacrylate) An opening 65 within said cap 60 of sufficient size and shape to allow a surgical instrument to pass provides instrument access through the cap 60, sheet or disc 41, and head 14. In a preferred embodiment, a shoulder 68 within said bore 66 of said cap 60 does not seat fully or intimately upon the sheet or disc 41. Instead, an approximately 0.005 inch gap 67 provides clearance whereby said sheet or disc 41 may elastically deform or move between the cap 60 and head 14 sandwich. Further alternative embodiments may place said gap between said sheet or disc and said head 14.

The composite valve 39 provides a passageway for a surgical instrument between said leaflets 49 while further sealing and preventing organ fluid leakage when the instrument is removed. Preferably the circumferential slot or groove 30 is placed in said cap 60 instead of the head 14 for the afore described alternative embodiment whereby a surgeon may manipulate the cannula 12 with a forceps or other surgical tool. The cannula tube 32 is placed and secured into said orifice 18 as described afore.

A further alternative embodiment places one or more notches or grooves 47 onto or into the shaft 43 of the obturator 42 utilized with the cannula 12. The notch or groove 47 allows the sheet 41 to have a reduced deformation while the shaft 43 is inserted through the cannual 12. That is, since the cannula 12 obturator 42 assembly may be stored in an assembled form for a period of time prior to a surgical procedure, the valve 39 must be stored in a form which will reduce deformation prior to use.

Further alternative embodiments may place said notches or grooves 47 onto the shaft of an instrument utilized with the valve 39. This notch 47 further serves as a seat for the valve 39 and assists in allowing cannula 12 sealing, especially for larger instrument shaft sizes. The method of use with the valve 39 is substantially equivalent as the preferred method of use with the added step of seating one or more of the valve 39 leaflets 49 with the obturator 42 or surgical instrument groove 47.

An embodiment of the present apparatus 10 cannula 12 for ophthalmic surgery utilizes a cannula tube 32 of approximately 0.25 inch length, 0.038 inch inside diameter 35, and a 0.001 inch wall thickness. The head 14 of the aforesaid ophthalmic surgery embodiment has a diameter of approximately 0.09 inch, length of approximately 0.07 inch and an orifice 18 of approximately 0.045 inch diameter. The blade portion 44 has a length of approximately 0.18 inch from the tip 58 through the base 55 at the bottom side 54 and 0.12 inch from the bump or protruded portion 46 through the base 55 at the top side 56, a width including said bump or protruded portion 46 of approximately 0.04 inch with said base 55 of approximately 0.036 inch, and a thickness of approximately 0.004 inch. The shaft 43 is approximately 0.038 inch in diameter and approximately 0.8 inch in length with said slit 52 having an approximate length of 0.08 inch and a width of 0.004 inch with said taper 53 of approximately seven degrees. The aforesaid dimension attributes are provided for enablement purposes only and are not intended to limit the scope and breadth of the present application.

Those skilled in the art will appreciate that a flexible walled cannula apparatus and method of use has been shown and described. The present invention is especially useful during so called minimally invasive surgeries. That is, the apparatus and method of use eliminates the prior art cannula hypodermic needle incision or trocar requirement, only requires a slit incision for placement, allows the cannula to seal when an instrument is removed, reduces the necessity for sutures after the cannula is removed, and further allows a surgeon to utilize instruments of a greater diameter while providing a self sealing substantially flat or linear incision. The present art further allows utilization of instruments having a greater head width than the cannula tube inside diameter during the surgical procedure. The apparatus and method of use is especially useful during ophthalmic surgery and other types of surgery which require minimally invasive surgical procedures.

Having described the invention in detail, those skilled in the art will appreciate that modifications may be made of the invention without departing from its spirit. Therefore, it is not intended that the scope of the invention be limited to the specific embodiments illustrated and described. Rather, it is intended that the scope of this invention be determined by the appended claims and their equivalents.

What is claimed is:

1. A flexible walled cannula comprising:
    a cannula having a head and a deformable cannula tube; and
    said head having a first proximal end and a second distal end and an orifice through said head from said first proximal end to said second distal end; and
    said deformable cannula tube having a substantially tube form which is elastically deformable and an inside diameter and an outside diameter smaller than a diameter of said orifice; and
    said deformable cannula tube mounted within at least a portion of said orifice and extending from said second distal end; and
    an obturator having a handle, a shaft mounted with said handle, and a blade portion mounted distally with said shaft; and
    said blade portion having a base, a dulled bottom side, and a top side having a dulled bump or protruded portion, a substantially distal cutting edge, and a width larger than said inside diameter of said cannula, and capable of creating a substantially flat or linear substantially self sealing incision of sufficient size to insert at least a portion of said cannula tube; and
    said cannula slidably placed onto said shaft with said shaft through said inside diameter and said obturator capable of removal from said cannula via deformation of said cannula tube and without cutting said cannula whereby a surgeon may form an incision within an anatomical organ with said cutting edge, insert said cannula tube into said organ through said incision, remove said obturator from said cannula with said dulled bottom side and dulled bump or protruded portion protecting said cannula tube from being cut, proceed with a surgery through said cannula, and there after remove said cannula and allow said incision to self seal without the use of sutures.

2. The flexible walled cannula as set forth in claim 1 further comprising:
    said outside diameter of said cannula tube sufficiently smaller than said diameter of said orifice whereby said cannula tube may elastically deform within said orifice of said head when said obturator is removed from said cannula without said blade portion cutting said cannula tube.

3. The flexible walled cannula as set forth in claim 2 further comprising: an adhesive between at least a portion of said cannula tube and said orifice.

4. The flexible walled cannula as set forth in claim 1 further comprising:
    a slightly flared or larger diameter cannula tube inside diameter nearest said first proximal end of said head whereby easy insertion of a surgical instrument is promoted.

5. The flexible walled cannula as set forth in claim 1 further comprising:
    a substantially circumferential slot or groove within said head of sufficient size to allow a forceps to grasp said slot or groove and to insert or remove said cannula.

6. The flexible walled cannula as set forth in claim 1 further comprising:
    a valve comprising a sheet of flexible material mounted with said head and having one or more cuts which form one or more leaflets which are capable of substantially preventing bodily fluid leakage from said inside diameter and said orifice.

7. The flexible walled cannula as set forth in claim 6 whereby said one or more cuts comprise:
    a semi circular cut; and
    a radial or linear cut.

8. The flexible walled cannula as set forth in claim 7 whereby said one or more cuts further comprise:
    said radial cut formed at an angle relative to the plane of said sheet whereby said leaflets overlap and ensure a seal.

9. The flexible walled cannula as set forth in claim 8 whereby said one or more cuts further comprise:
    said radial or linear cut extended to an edge or periphery of said sheet.

10. The flexible walled cannula as set forth in claim 6 further comprising:
    a cap having a bore of sufficient size to mate over said first proximal end of said head, a shoulder within said bore, and an opening within said cap of sufficient size and shape to allow a surgical instrument to pass; and
    said sheet positioned substantially between said shoulder and said first proximal end and said cap attached with said head.

11. The flexible walled cannula as set forth in claim 10 further comprising:
    a bevel within said orifice substantially at said first proximal end of said head whereby a clearance is provided for said sheet when said surgical instrument is passed through said valve.

12. The flexible walled cannula as set forth in claim 11 further comprising:

a gap between said sheet and said cap or said head which provides clearance whereby said sheet may elastically deform.

13. A flexible walled cannula comprising:
a cannula having a round button shaped head and a cannula tube; and
said head having a first proximal end and a second distal end and an orifice from said first proximal end to said second distal end; and
a cannula tube having a substantially flexible tube form and an inside diameter and an outside diameter less than a diameter of said orifice; and
at least a portion of said cannula tube adhesively bonded with said orifice; and
at least a portion of said cannula tube inside diameter nearest said first proximal end having a larger diameter than said cannula tube inside diameter distal thereto; and
an obturator having a shaft onto which said cannula is slidably placed, a handle, and a blade portion mounted with said shaft; and
said blade portion of a substantially flat form having a base positioned within a slit within said shaft, a dulled bottom side, a top side having a bump or protruded portion, and a distal cutting edge with a tip; and
said shaft having a distal taper nearest said blade portion whereby said blade portion is capable of forming a substantially flat self sealing incision within a bodily organ and said cannula is capable of sliding on said shaft into said incision and said obturator is capable of removal from said cannula without cutting said cannula.

14. The flexible walled cannula as set forth in claim 13 further comprising:
a valve mounted with said head and capable of sealing said orifice and said inside diameter from a bodily fluid leakage.

15. The flexible walled cannula as set forth in claim 14, said valve further comprising:
a sheet or disc having one or more cuts which form leaflets, said sheet or disc mounted upon said first proximal end of said head; and
a cap having a bore positioned around at least a portion of said first proximal end of said head and an opening; and
said sheet or disc sandwiched between said cap and opening and said head.

16. The flexible walled cannula as set forth in claim 15, said one or more cuts further comprising:
a semi-circular cut and a radial or linear cut extending from said semi-circular cut.

17. A method of utilizing a flexible walled cannula in conjunction with a substantially self sealing incision, the steps comprising:
forming a cannula having a head with an orifice and a deformable cannula tube having an outside diameter less than a diameter of said orifice; and
mounting a portion of said cannula tube within said orifice whereby said cannula tube may deform within said head and a remainder of said cannula tube extends from said head; and
forming an obturator having a handle, attaching a shaft with said handle, and attaching a blade portion distally with said shaft; and
forming a distal cutting edge and a tip capable of creating a substantially flat incision onto said blade portion and further forming a width of said blade portion greater than an inside diameter of said cannula tube; and
forming a dulled bottom side and a protruded top side onto said blade portion; and
observing while inserting said obturator into a proximal end of said head and into said cannula tube; and
deforming said cannula tube within said orifice of and external to said head as said blade portion of said obturator passes through said cannula tube and said dulled sides avoid cutting said cannula tube; and
positioning said blade portion distal to said head and said cannula tube; and
grasping said handle and forming a substantially flat incision with said blade portion within an anatomical organ; and
forming said incision into said organ of a sufficient width to accept at least a portion of said cannula tube external to said head; and
sliding said cannula toward and into said incision while said obturator is retained within said incision; and
removing said obturator from said cannula and allowing said dulled sides to deform said inside diameter of said cannula tube without cutting said cannula tube; and
allowing said cannula tube to deform and at least partially seal within said incision; and
inserting one or more surgical instruments into and through said cannula; and
performing a surgical procedure with said one or more instruments; and
removing said cannula from said incision; and
allowing said incision to substantially self seal.

18. The method of utilizing a flexible walled cannula in conjunction with a substantially self sealing incision as set forth in claim 17, the steps further comprising:
forming a valve at said proximal end of said head by sandwiching a flexible sheet or disc between said head and a cap; and
cutting said flexible sheet to form leaflets between which said obturator may be placed when inserting and removing; and
allowing said leaflets to seat after removing said obturator and prevent fluid leakage from said organ.

19. The method of utilizing a flexible walled cannula in conjunction with a substantially self sealing incision as set forth in claim 18, the steps further comprising:
forming one or more notches or grooves onto said shaft of said obturator; and
seating said leaflets into said notches or grooves whereby said valve maintains a relaxed position prior to forming said incision.

* * * * *